(12) United States Patent
Johnson

(10) Patent No.: US 11,484,877 B2
(45) Date of Patent: *Nov. 1, 2022

(54) BLOOD METERING DEVICE WITH DESICCANT AND SUPPORT FOR STORAGE MEDIA AND INLAY WITH FLANGE

(71) Applicant: WEAVR HEALTH CORP., Cambridge, MA (US)

(72) Inventor: Brandon T. Johnson, Cambridge, MA (US)

(73) Assignee: WEAVR HEALTH CORP., Cambridge, MA (US)

( * ) Notice: Subject to any disclaimer, the term of this patent is extended or adjusted under 35 U.S.C. 154(b) by 477 days.

This patent is subject to a terminal disclaimer.

(21) Appl. No.: 16/421,619

(22) Filed: May 24, 2019

(65) Prior Publication Data

US 2019/0381499 A1 Dec. 19, 2019

Related U.S. Application Data

(63) Continuation-in-part of application No. 16/167,623, filed on Oct. 23, 2018, now Pat. No. 11,358,139, and
(Continued)

(51) Int. Cl.
*A61B 5/15* (2006.01)
*B01L 3/00* (2006.01)
*G01N 1/10* (2006.01)

(52) U.S. Cl.
CPC ............. *B01L 3/5023* (2013.01); *G01N 1/10* (2013.01); *B01L 2200/16* (2013.01);
(Continued)

(58) Field of Classification Search
CPC combination set(s) only.
See application file for complete search history.

(56) References Cited

U.S. PATENT DOCUMENTS 3,430,813 A 3/1969 Gilmont et al.
3,767,085 A 10/1973 Cannon et al.
(Continued)

FOREIGN PATENT DOCUMENTS

EP 2772306 A1 9/2014
EP 3088083 B1 11/2016
(Continued)

OTHER PUBLICATIONS

International Search Report and Written Opinion dated Aug. 20, 2019; Appl. No. PCT/US2019/033878.
(Continued)

*Primary Examiner* — Paul S Hyun
(74) *Attorney, Agent, or Firm* — Wilson Sonsini Goodrich & Rosati

(57) ABSTRACT

A blood sample collection and/or storage device includes a two-piece housing that encompasses a port at which a fingertip blood sample is collected at a sample port. After the sample is taken, the two-piece housing is moved to a closed position deposit the sample onto a storage membrane Embodiments of the device include a one or more capillaries with movable plungers that dispense fluid from the sample port onto the membrane as the housing is closed. A desiccant, which may be held in place by a backbone structure within the housing, is positioned adjacent the membrane. The housing may also be opened to access the stored sample for further processing.

19 Claims, 14 Drawing Sheets

Related U.S. Application Data a continuation-in-part of application No. 16/164,988, filed on Oct. 19, 2018, now Pat. No. 11,358,138.

(60) Provisional application No. 62/677,209, filed on May 29, 2018.

(52) U.S. Cl.
CPC . *B01L 2300/045* (2013.01); *B01L 2300/0816* (2013.01); *B01L 2300/161* (2013.01); *B01L 2400/0406* (2013.01); *B01L 2400/0475* (2013.01)

(56) References Cited

U.S. PATENT DOCUMENTS

| | | | |
|---|---|---|---|
| 4,185,628 A | 1/1980 | Kopfer | |
| 4,257,267 A | 3/1981 | Parsons | |
| 4,386,606 A | 6/1983 | Tretinyak et al. | |
| 4,558,793 A | 12/1985 | Hansen | |
| D284,214 S | 6/1986 | Hatcher et al. | |
| 4,690,005 A | 9/1987 | Tervamaki et al. | |
| 4,915,695 A | 4/1990 | Koobs | |
| 5,013,667 A | 5/1991 | Lynn et al. | |
| D324,426 S | 3/1992 | Fan et al. | |
| D331,807 S | 12/1992 | Sodergren | |
| 5,339,830 A | 8/1994 | Blake, III | |
| 5,384,264 A | 1/1995 | Chen et al. | |
| 5,504,011 A | 4/1996 | Gavin et al. | |
| 5,518,006 A | 5/1996 | Mawhirt et al. | |
| D410,287 S | 5/1999 | Von Boetticher | |
| D411,621 S | 6/1999 | Eisenbarth et al. | |
| 6,093,156 A | 7/2000 | Cunningham et al. | |
| 6,106,779 A | 8/2000 | Buechler et al. | |
| 6,120,733 A | 9/2000 | Goodman et al. | |
| 6,372,514 B1 | 4/2002 | Lee | |
| 6,399,398 B1 | 6/2002 | Cunningham et al. | |
| 6,524,864 B2 | 2/2003 | Fernandez Decastro | |
| D512,512 S | 12/2005 | Bell et al. | |
| 7,404,931 B2 | 7/2008 | Frey et al. | |
| 7,435,237 B2 | 10/2008 | Tan | |
| D590,063 S | 4/2009 | Garthoff et al. | |
| 7,803,319 B2 | 9/2010 | Yang et al. | |
| 7,838,258 B2 | 11/2010 | Yang et al. | |
| D631,556 S | 1/2011 | Shi et al. | |
| 8,105,554 B2 | 1/2012 | Kanigan et al. | |
| 8,173,380 B2 | 5/2012 | Yang et al. | |
| 8,206,650 B2 | 6/2012 | Samsoondar | |
| 8,329,119 B2 | 12/2012 | Pearcy et al. | |
| D676,145 S | 2/2013 | Kouge et al. | |
| 8,561,795 B2 | 10/2013 | Schott | |
| 8,741,230 B2 | 6/2014 | Holmes et al. | |
| 8,808,202 B2 | 8/2014 | Brancazio | |
| 8,821,412 B2 | 9/2014 | Gonzalez-Zugasti et al. | |
| 8,827,971 B2 | 9/2014 | Gonzalez-Zugasti et al. | |
| 8,940,539 B2 | 1/2015 | Pearcy et al. | |
| 8,976,983 B2 | 3/2015 | Jang et al. | |
| D728,818 S | 5/2015 | Burroughs et al. | |
| 9,023,292 B2 | 5/2015 | Rostaing et al. | |
| 9,033,898 B2 | 5/2015 | Chickering, III et al. | |
| 9,040,236 B2 | 5/2015 | Hill et al. | |
| 9,041,541 B2 | 5/2015 | Levinson et al. | |
| D733,313 S | 6/2015 | Kouge et al. | |
| D734,482 S | 7/2015 | Peterman et al. | |
| 9,113,836 B2 | 8/2015 | Bernstein et al. | |
| 9,119,578 B2 | 9/2015 | Haghgooie et al. | |
| 9,176,126 B2 | 11/2015 | Holmes et al. | |
| 9,289,763 B2 | 3/2016 | Berthier et al. | |
| 9,295,417 B2 | 3/2016 | Haghgooie et al. | |
| 9,386,948 B2 | 7/2016 | Holmes et al. | |
| 9,427,184 B2 | 8/2016 | Holmes et al. | |
| 9,636,062 B2 | 5/2017 | Holmes et al. | |
| 9,987,629 B2 | 6/2018 | Berthier et al. | |
| D822,275 S | 7/2018 | Moon et al. | |
| D824,530 S | 7/2018 | Velschow et al. | |
| D855,210 S | 7/2019 | Ito et al. | |
| D861,189 S | 9/2019 | Lampropoulos et al. | |
| D861,915 S | 10/2019 | Zakrys et al. | |
| 10,488,424 B2 | 11/2019 | Steckl et al. | |
| 10,545,140 B2 | 1/2020 | Cheng et al. | |
| 10,597,651 B2 | 3/2020 | Pottathil | |
| D894,422 S | 8/2020 | Johnson | |
| D895,140 S | 9/2020 | Heron | |
| D895,146 S | 9/2020 | Osmus et al. | |
| 2002/0031839 A1 | 3/2002 | McNeirney et al. | |
| 2002/0173047 A1 | 11/2002 | Hudak et al. | |
| 2003/0235825 A1 | 12/2003 | Shea et al. | |
| 2004/0082878 A1 | 4/2004 | Baldwin et al. | |
| 2005/0119589 A1 | 6/2005 | Tung et al. | |
| 2005/0232813 A1 | 10/2005 | Karmali | |
| 2006/0228259 A1 | 10/2006 | Samsoondar | |
| 2007/0184547 A1 | 8/2007 | Handique et al. | |
| 2008/0025872 A1 | 1/2008 | Dykes et al. | |
| 2008/0118399 A1 | 5/2008 | Fleming | |
| 2008/0145835 A1 | 6/2008 | Alajem et al. | |
| 2009/0117665 A1 | 5/2009 | Tung et al. | |
| 2010/0099112 A1 | 4/2010 | Zhou et al. | |
| 2010/0210970 A1 | 8/2010 | Horikawa et al. | |
| 2010/0222703 A1 | 9/2010 | Takashima et al. | |
| 2011/0124984 A1 | 5/2011 | Rostaing | |
| 2011/0127294 A1 | 6/2011 | Pearcy et al. | |
| 2011/0143365 A1 | 6/2011 | Buchanan | |
| 2011/0152720 A1 | 6/2011 | Zappia et al. | |
| 2011/0212453 A1 | 9/2011 | Agarwal et al. | |
| 2012/0168305 A1 | 7/2012 | Hunter | |
| 2013/0171044 A1 | 7/2013 | Nikonorov et al. | |
| 2013/0172698 A1 | 7/2013 | Reynolds et al. | |
| 2013/0211289 A1 | 8/2013 | Moga et al. | |
| 2013/0247694 A1 | 9/2013 | Chen et al. | |
| 2013/0280725 A1 | 10/2013 | Ismagilov et al. | |
| 2013/0309679 A1 | 11/2013 | Ismagilov et al. | |
| 2014/0050620 A1 | 2/2014 | Johnson et al. | |
| 2014/0073990 A1 | 3/2014 | Holmes et al. | |
| 2014/0273058 A1* | 9/2014 | Menon | G01N 1/405 435/29 |
| 2014/0303518 A1 | 10/2014 | Pierce et al. | |
| 2014/0323911 A1 | 10/2014 | Sloan et al. | |
| 2014/0329258 A1 | 11/2014 | Fleming | |
| 2015/0069072 A1 | 3/2015 | Kelley et al. | |
| 2015/0231627 A1 | 8/2015 | Sloan et al. | |
| 2015/0273467 A1 | 10/2015 | Sloan et al. | |
| 2015/0346105 A1 | 12/2015 | Gutsell et al. | |
| 2016/0051981 A1 | 2/2016 | Berthier et al. | |
| 2016/0349156 A9 | 12/2016 | Menon et al. | |
| 2017/0023546 A1 | 1/2017 | Holmes et al. | |
| 2017/0042460 A1 | 2/2017 | Holmes et al. | |
| 2017/0108477 A1 | 4/2017 | Ozbal | |
| 2017/0176306 A1 | 6/2017 | Boehm et al. | |
| 2017/0227536 A1 | 8/2017 | Matsuura | |
| 2018/0043358 A1 | 2/2018 | Fujimoto | |
| 2018/0356393 A1 | 12/2018 | Piasio et al. | |
| 2019/0111421 A1 | 4/2019 | Johnson | |
| 2019/0126266 A1 | 5/2019 | Johnson | |
| 2020/0121234 A1 | 4/2020 | Johnson | |
| 2020/0206743 A1 | 7/2020 | Johnson | |

FOREIGN PATENT DOCUMENTS

| | | |
|---|---|---|
| WO | WO-0167111 A2 | 9/2001 |
| WO | WO-03023371 A1 | 3/2003 |
| WO | WO-2012003306 A1 | 1/2012 |
| WO | WO-2017075050 A1 | 5/2017 |
| WO | WO-2017123668 A1 | 7/2017 |

OTHER PUBLICATIONS

"Syringe Selection Guide, Complete Guide to Selecting the Right Hamilton Microliter, Gaslight, and Specialty Syringes for Your Application", Hamilton, pp. 1-24, 2017.
1/1-Designs Questel. APN—3020160043209 (2019.).
A new era for blood collection and testing. Online, published date unkown. Retrieved on Nov. 18, 2019 from URL https://www.bostonmicrofluidics.com/.

(56) References Cited

OTHER PUBLICATIONS

Buckle. Online, published date Jun. 5, 2016. Retrieved on Nov. 22, 2019 from URL: http://www.8472.co.uk/misc_buckles_double.htm.
Garden House/Joaqufn Alvado Banon. Online, published date 2012. Retrieved on Nov. 22, 2019 from URL: https://www.archdaily.com/306750/garden-house-joaquin-alvado-banon.
PCT/US2018/056629 International Search Report and Written Opinion dated Jan. 22, 2019.
PCT/US2019/033879 International Search Report and Written Opinion dated Oct. 25, 2019.
PCT/US2019/056918 International Search Report and Written Opinion dated Jan. 27, 2020.
PCT/US2019/056926 International Search Report and Written Opinion dated Jan. 24, 2020.
PCT/US2019/056930 International Search Report and Written Opinion dated Jan. 9, 2020.
PCT/US2020/049460 International Search Report and Written Opinion dated Feb. 19, 2021.
Through the isosceles trapezoid window. Online, published date Dec. 6, 2006. Retrieved on Nov. 22, 2019 from URL: https://www.flickr.com/photos/page94/315753467.
U.S. Appl. No. 16/164,988 Non-Final Office Action dated Jul. 20, 2021.
U.S. Appl. No. 16/167,623 Non-Final Office Action dated Oct. 22, 2021.
U.S. Appl. No. 16/657,041 Non-Final Office Action dated Sep. 21, 2021.
U.S. Appl. No. 16/657,101 Non-Final Office Action dated Oct. 6, 2021.
U.S. Appl. No. 16/777,959 Final Office Action dated Aug. 10, 2021.
U.S. Appl. No. 16/242,084 Non-Final Office Action dated Jul. 16, 2021.

\* cited by examiner

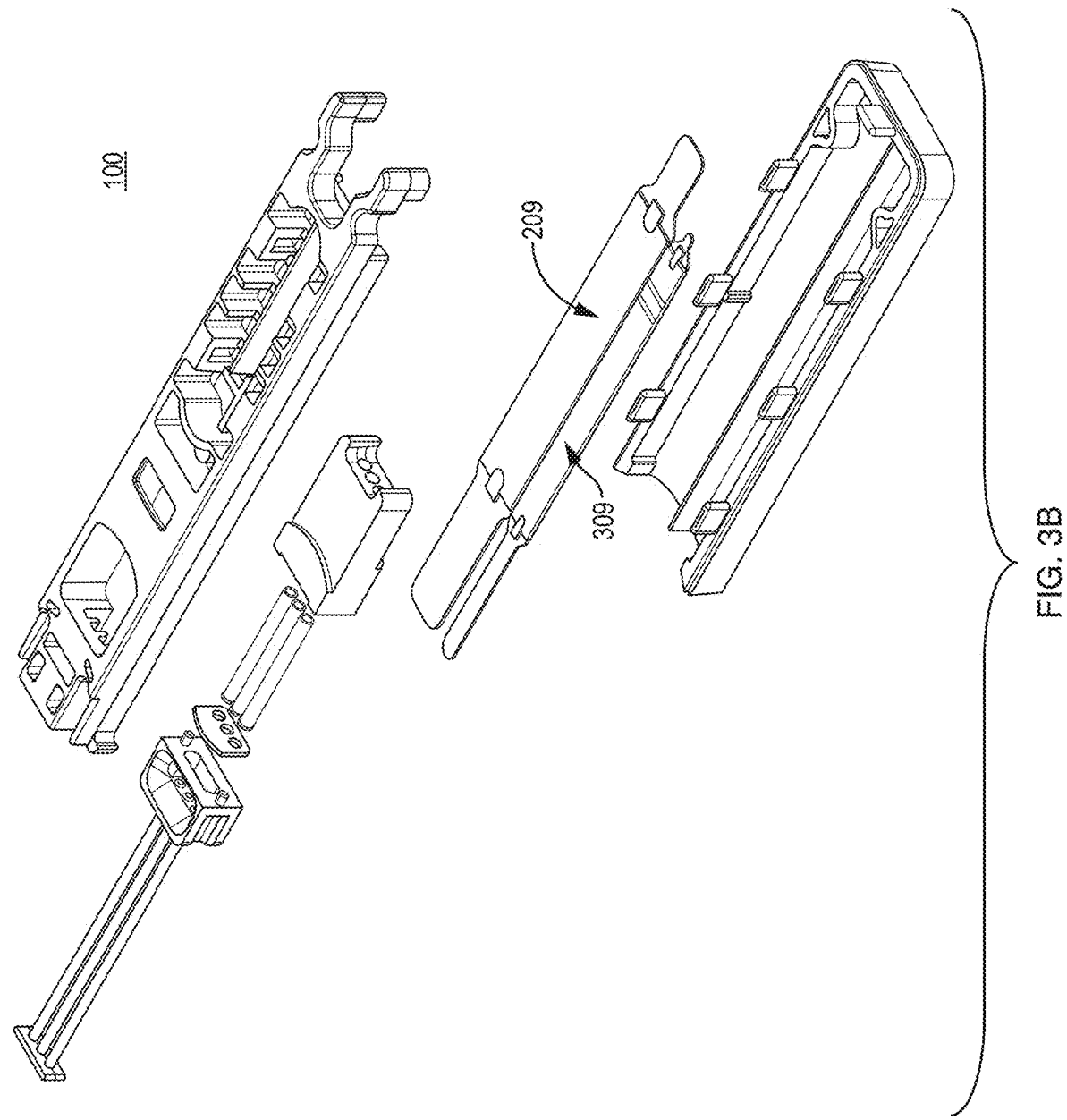

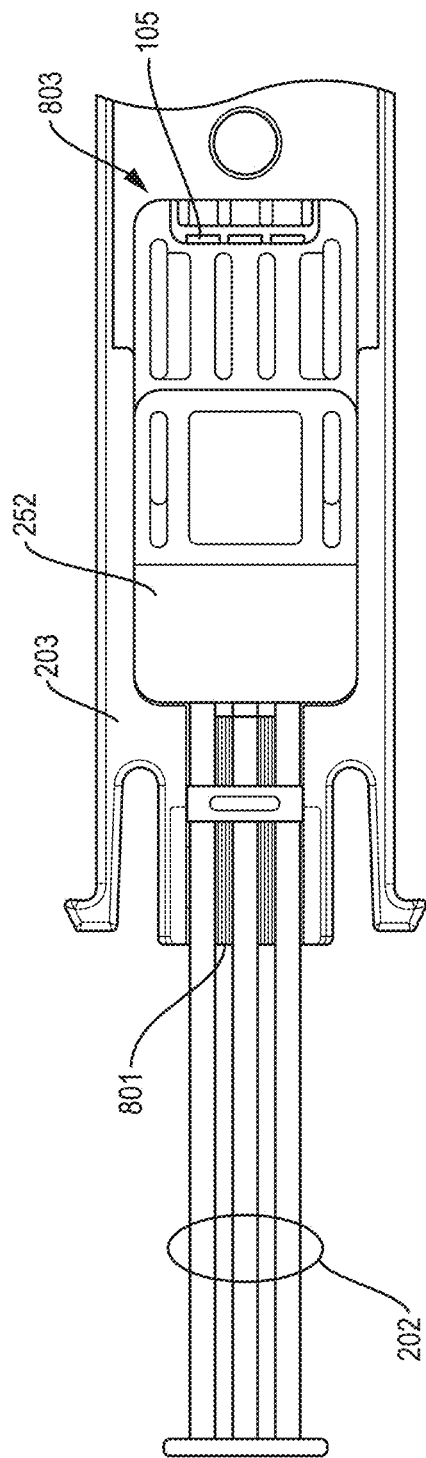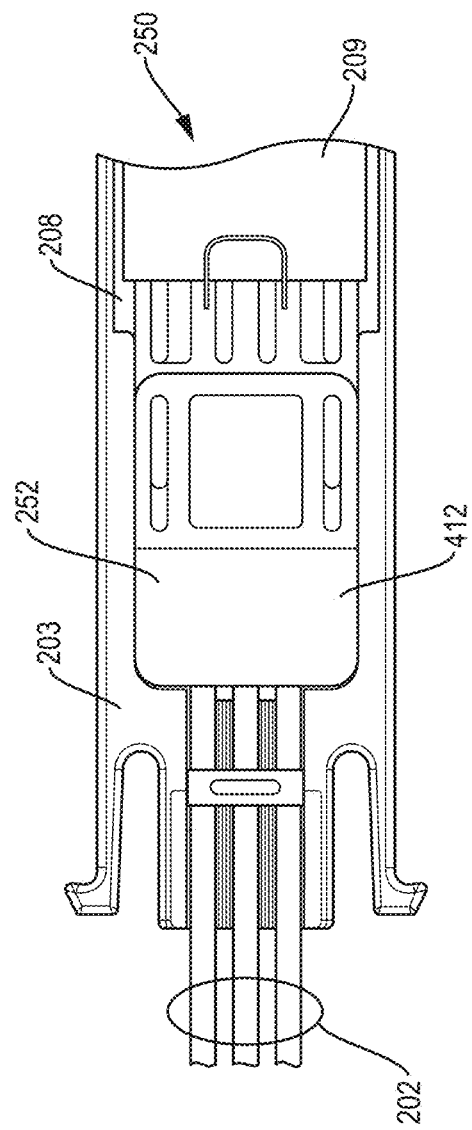
FIG. 8
FIG. 9

BLOOD METERING DEVICE WITH DESICCANT AND SUPPORT FOR STORAGE MEDIA AND INLAY WITH FLANGE

CROSS REFERENCE TO RELATED APPLICATIONS

This application claims priority to a U.S. Provisional Patent Application Ser. No. 62/677,209 filed May 29, 2018 entitled "Blood Metering Device with Desiccant and Support for Storage Media and Inlay with Flange", and U.S. patent application Ser. No. 16/164,988 filed Oct. 19, 2018 entitled "Fluid Sample Collection Device", and U.S. patent application Ser. No. 16/167,623 filed Oct. 23, 2018 entitled "Pinch to Open Sample Collection Device". The entire contents of each of the above-referenced applications are hereby incorporated by reference.

BACKGROUND

Technical Field

This patent relates to devices and methods for body fluid sample collection.

Background Information

Blood used for diagnostic testing is most often extracted from a patient with a hypodermic needle and collected in a test tube. The collected blood is then packaged for shipment to a remote lab where various diagnostic tests are performed. However, many diagnostic tests require significantly less volume than the actual collected sample. Separation of cellular components from the sample is also needed for some tests.

Many tests only require small blood samples, where a finger stick rather than a hypodermic needle can produce enough blood. But this small amount of blood cannot be easily transported to a remote lab. If the testing method cannot be immediately used at the same time the blood is extracted, convenient and reliable methods of collecting, prepping, and preserving small amounts of blood are still needed.

US Patent Publication US2014/0050620A1, assigned to Boston Microfluidics, Inc., describes several ways to implement a portable, user-friendly device for collecting a biological fluid sample and stabilizing it for transport to a remote lab. The devices include a small, hand-held housing that provides a chamber for collecting a fluid sample. Movement of the housing itself, and/or mechanisms located within the housing, initiate collection of a predetermined, metered volume of a fluid sample. The devices may also stabilize the collected sample and/or seal the sample in the chamber. Other mechanisms in the device may mix the collected sample with a reagent.

SUMMARY

A sample collection device can be used to collect, meter, and heparinize a body fluid sample. Fluid collected from a patient is first introduced into the device via a sample port, such as by directing blood droplets from a fingertip into a well. In some configurations, metering capillaries then extract blood from the sample port and deposit it onto a storage media via capillary action. In addition, one or more plungers, coupled to a closeable housing, may further encourage dispensing fluid from the metering capillaries and onto the storage media. The plungers may be attached to one or more movable housing pieces, such that when the housing is moved from an open to a closed position, the plungers are forced through the capillaries.

Some embodiments of the device include a stabilization agent arranged to engage the fluid as the one or more plungers dispense fluid onto the membrane. The stabilization agent may be heparin and/or EDTA. The stabilization agent may be coated or deposited onto an interior of at least one of the capillaries or the plungers or the storage membrane. This configuration may also include a desiccant located adjacent the membrane.

In some arrangements, an assay region may also be located between the capillaries and the membrane, such that the stored reagent is mixed with the fluid when the housing is moved from the open position to the closed position.

A raised ridge portion may be provided adjacent the well. The ridge provides a convenient place to wipe a patient's finger to encourage blood droplets to better flow.

The housing may also include one or more windows positioned on the housing in a location such that at least a portion of the capillaries and/or sample media are visible through the window.

A first housing section and second housing section may engage and slide along a center support section, to allow moving the housing from the open position to the closed position, and thus push the plungers through the capillaries. In that configuration, the center support section may include an opening for the insert element that defines the sample well.

The sample well may be defined by an inlay element disposed within the housing. In that case, the inlay may also provide the raised ridge portion. The inlay typically further includes one or more thru holes, each for holding a respective one of capillaries in a defined position. The inlay piece can also be used to retain at least one capillary in alignment with at least one of the plungers as the housing is moved from the open position to the closed position.

The inlay element may also include a slot disposed at an exit port of the one or more capillaries. The slot provides a directed path for blood exiting the capillaries onto the storage media.

The capillaries and/or an inlay part that provides the sample well and supports the capillaries may also be wholly or partially transparent. These design feature can provide further visible confirmation that a sample of blood fluid is properly collected and/or stored.

The plungers can be connected to a tab attachment on an end distal from the capillaries. The tab can be disposed adjacent one of the housing pieces, so that the plungers are forced into the capillaries as the housing is closed.

A ratcheting mechanism may be located at one end of the backbone, to further assist with holding the housing in the closed position during transit. That mechanism may be engaged when the housing is moved from the open to the closed position. In some embodiments, access holes are provided at one end of the housing, a tool to more easily disengage the ratcheting mechanism, and pry open the housing to gain access to the stored blood sample.

The storage media may take different forms. For example, it may be a substrate having a pair of engagement tabs therein and spaced apart from one another. The blood sample collection storage media is then disposed on the substrate and sized to fit between the engagement tabs.

BRIEF DESCRIPTION OF THE DRAWINGS

FIG. 3B is an exploded view of another example device with two membranes.

FIG. 8 is a view of the bottom with housing covers and media support removed.

FIG. 9 is a similar view of the bottom but with the media support in place.

DETAILED DESCRIPTION OF PREFERRED EMBODIMENTS

Figure 1:
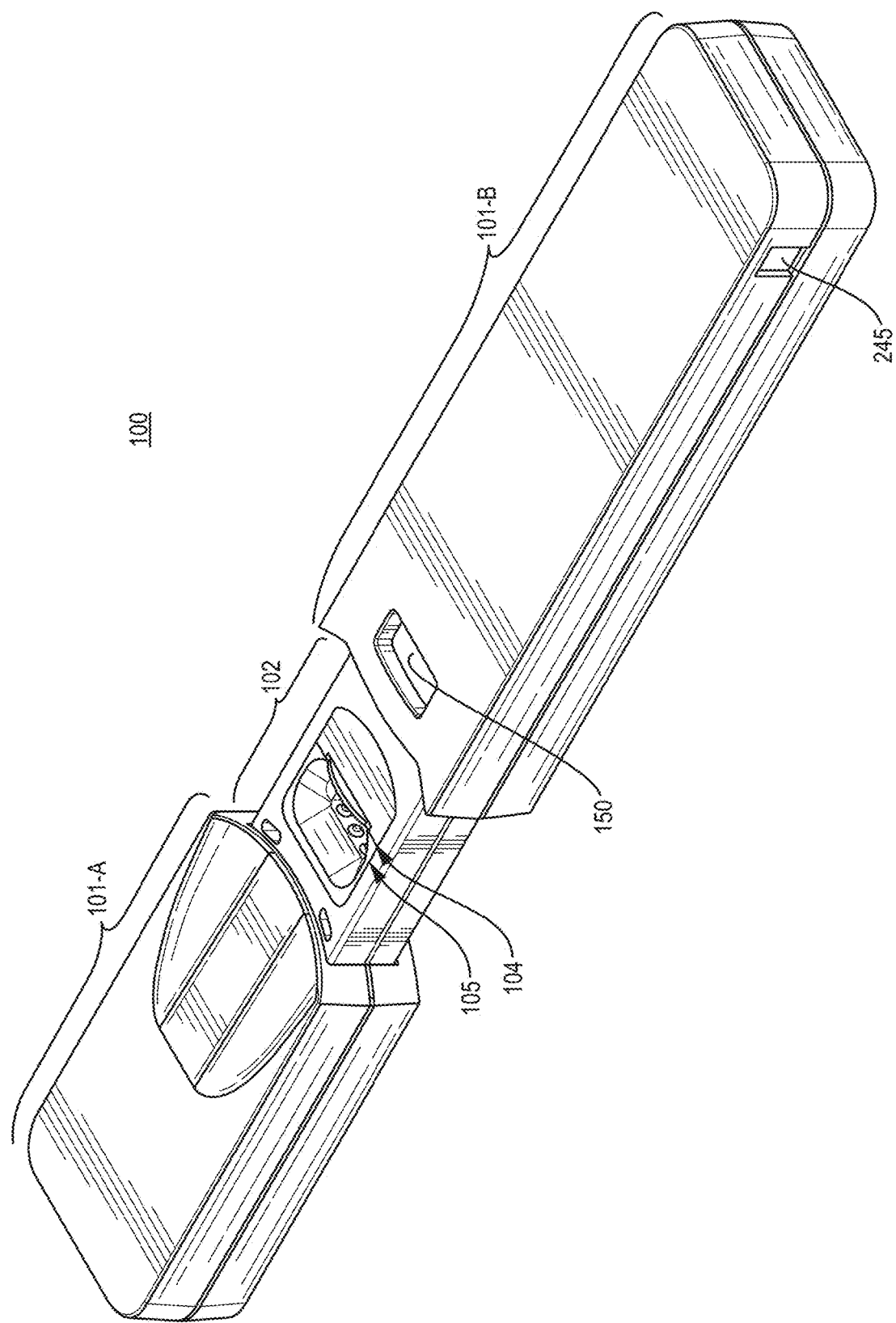
FIG. 1 is an isometric view of a blood sample collection device in the open position, before it is used.

FIG. 1 is an isometric view of an example fluid collection device 100. The device 100 includes a two-piece housing 101 that supports and encloses a fluid sample port 102. The housing 101 includes a first housing piece 101-A and second housing piece 101-B. In this view, the housing is in the open position with the two housing pieces 101-A, 101-B spaced apart from one another, to provide access to the sample port 102. A sample collection well 104 and one or more capillaries 105 located adjacent the sample port 102 are partially visible in this figure. A window 150 in the housing permits a user to confirm the status of one or more portions of a fluid sample in the process of being collected and/or stored within the device 100.

Figure 2:
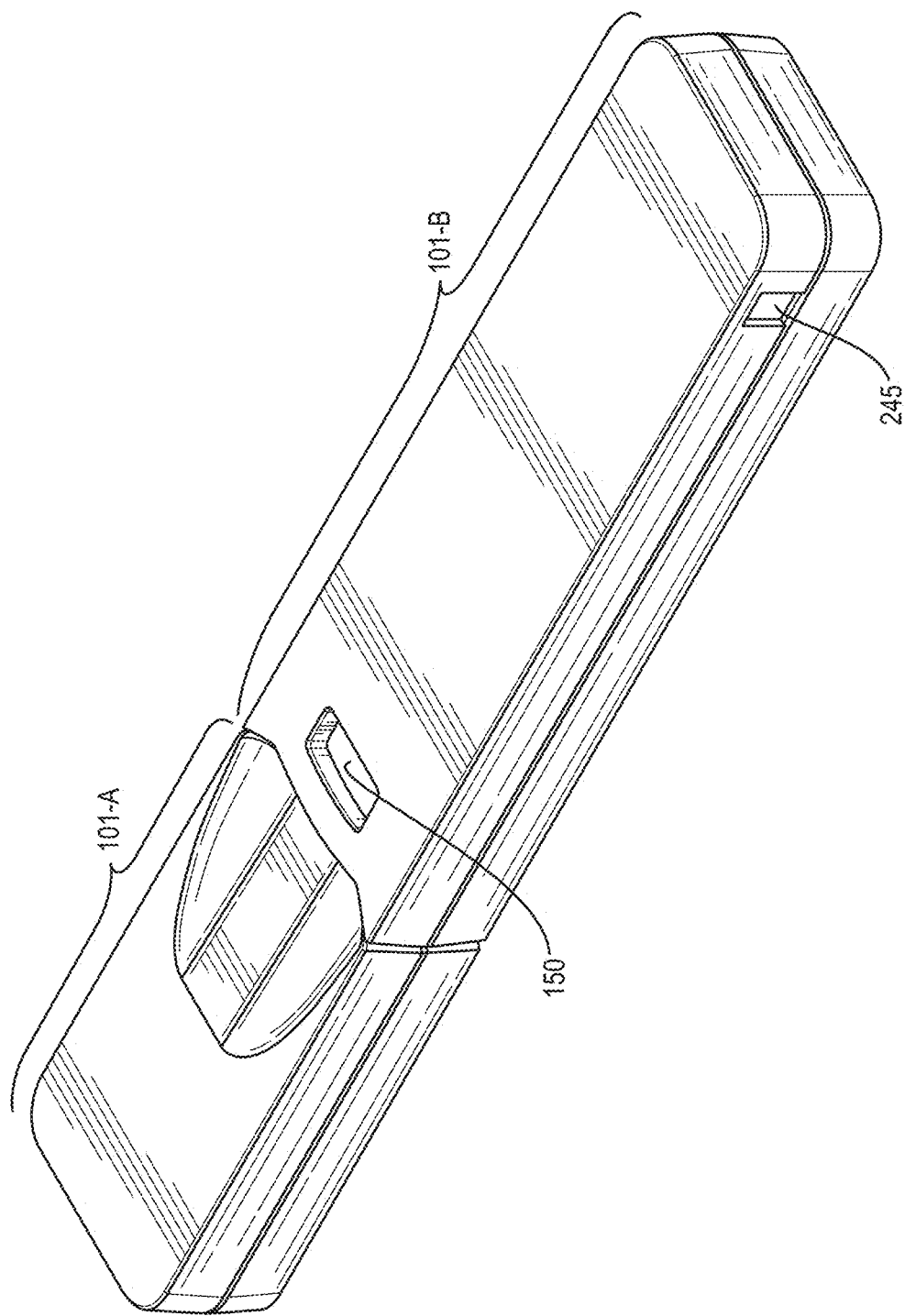
FIG. 2 is a view of the collection device in the closed position.

FIG. 2 is a similar isometric view of the device 100. In this view, a blood sample has been taken via the sample port 102, and the two housing pieces 101-A and 101-B have been pushed together to place the device 100 in a closed position. In this closed position, the window 150 still provides access to the blood collection status.

The device 100 is typically used to collect a blood sample as follows. The device 100 is initially presented in its open position, as per FIG. 1, to provide access to the well 104. A user, such as a patient herself or a health care professional, then uses a lancet to produce a blood sample such as from a fingertip. Drops of whole blood are then taken with the finger positioned near to, above, adjacent to, or even in contact with the well 104 or other parts of the sample port 102 to minimize blood spillage.

Blood is then eventually drawn into the rest of the device 100 in one or more different ways. As will be explained in more detail below for one embodiment, blood flows and/or is first drawn from the well 104 by one or more collection capillaries 105 adjacent the sample port via capillary action.

The capillaries may be visibly transparent so that the user can confirm that blood is being properly drawn into the device 100. The capillaries 105 can optionally be pre-coated with reagents such as heparin and/or EDTA for subsequent stabilization and preservation of the sample. The capillaries 105 can also have a known and predetermined volume, in which case the incoming sample is precisely metered. The collection capillaries 105 then direct the metered sample to a media inside the device housing 101

The user, who can be the patient himself/herself or a healthcare professional, then manually closes the device 100 by pushing the two housing pieces 101-A, 101-B together, resulting in the housing position shown in FIG. 2. As more fully explained below, the motion associated with closing the housing may then optionally enact one or more mechanisms that further process the sample, and to securely store it inside the device 100.

The window 150 may include a transparent piece of material that enables the user to view the state of the sample port 102, the well 104, and/or collection capillaries 105. In that way, an indication of whether a sufficient sample of blood is being drawn into the device 100 (when the housing 101 is in the open position of FIG. 1) or was drawn into the device (when the housing 101 is in the closed position as in FIG. 2).

Figure 3A:
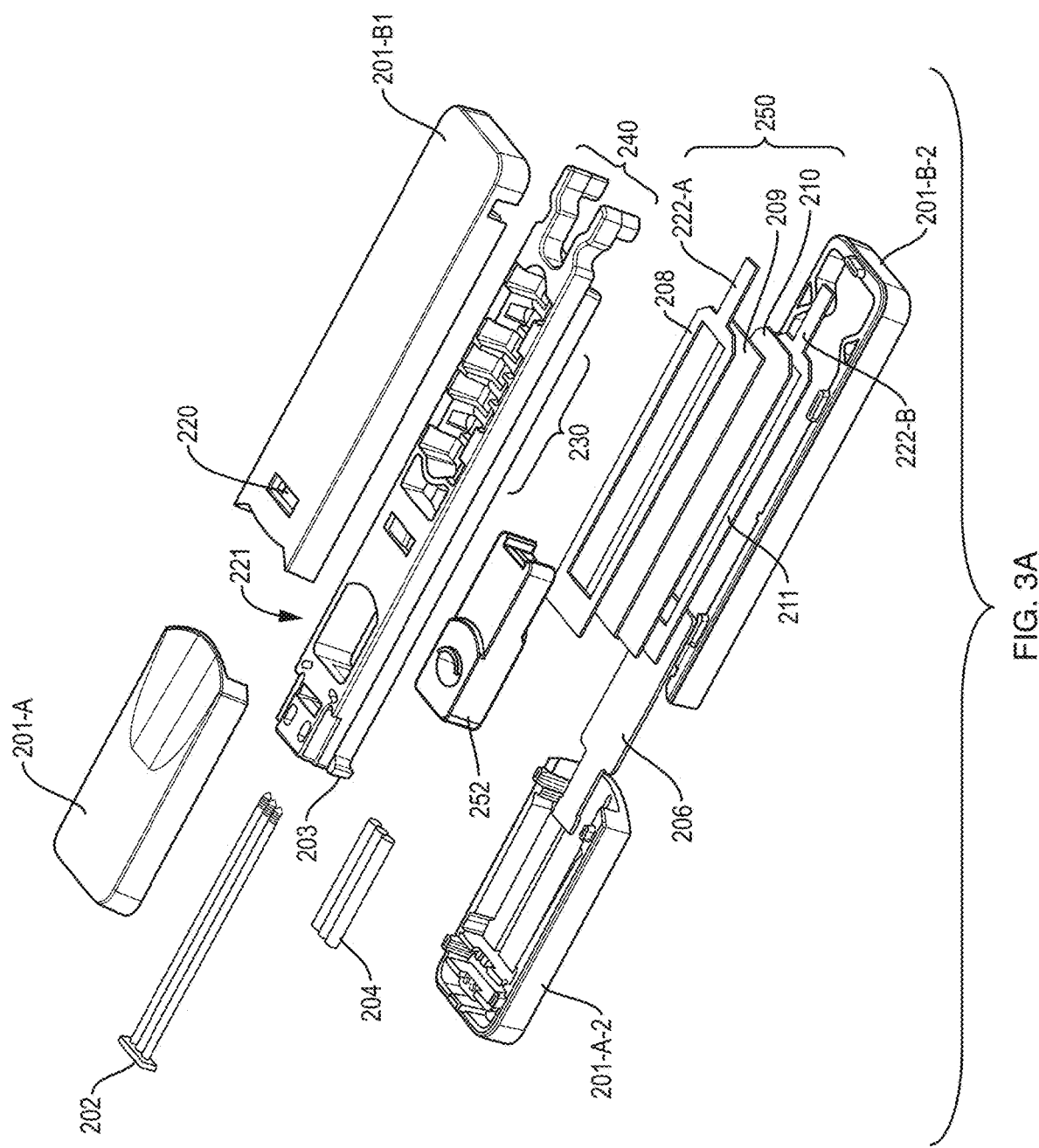
FIG. 3A is an exploded view showing components of one example of the collection device.

FIG. 3A is a more detailed, exploded view of the components of the device 100. The first housing piece 101-A consists of a top case 201-A-1 and bottom case 201-A-2, and second housing piece 101-B consists of a top case 201-B-1 and bottom case 201-B-2.

A backbone structure 203 provides a support for the two housing pieces 101-A, 101-B. The inside vertical walls of the housing pieces 201-A, 201-B may engage elongated slots or other structures formed in the backbone 203, thus enabling at least second housing piece 101-B to slide back and forth along the backbone, and to thus move the housing into the open or closed position. In one arrangement, first housing piece 101-A remains fixed in position on backbone 203. However other embodiments are possible where first housing piece 101-A slides on backbone 203 and second housing piece 101-B remains fixed, or where both housing pieces 101-A, 101-B can slide with respect to one another.

The backbone 203 also supports other components of the device 100. For example, the backbone 203 provides a location for the sample collection port 102, as formed from an inlay part (also referred to as a capillary support element) 252. A plunger rack 202 is also supported by the backbone 203. The backbone 203 may further include a ribbed section 230 to support a desiccant tablet (not shown in FIG. 3) to further dry the collected sample. The backbone 203 may also have tines at an end that provide a ratcheting closure 240, which is activated when the two housing pieces 101-A, 101-B are pushed together.

Capillaries 204 (also referred to with reference number 105 in other figures) are inserted into and held in place by longitudinal holes (not shown in FIG. 3) formed in the inlay 252. The capillaries and may be formed as a rigid tube of precisely defined volume, in which case they also serve a metering function. The capillaries 204 extract a defined quantity of blood by engagement with the blood in the sample collection port 102 through capillary action. The inlay 252 may fit into a hole 221 in backbone 203. As explained in further detail below, the inlay 252 defines the location of a well 104 into which the patient's blood is introduced.

The capillaries 204 can optionally be pre-coated with reagents, heparin, EDTA, or other substances.

One or more capillaries 204 may also store a predetermined amount of a liquid reagent. Such a reagent may then be dispensed together or in parallel with the blood sample when the housing is moved from the open to the closed position. However, reagents of other types may also be located in a storage region within the housing. The storage region (not designated in the figures), may hold a first type of reagent such as a solid surface or substrate, and a second type being a liquid storage chamber, each of which are placed in the path of the blood sample collected by the device 100.

In one arrangement, the one or more plungers 202 firmly engage with the inner diameter of the capillaries 204, creating a shutoff that blocks off any excess blood sample while also pushing the metered sample volume to the subsequent downstream processing steps.

A base 206 may also fit into the backbone 203 to provide additional mechanical support for a blood collection element 250. The collection element 250 may consist of a sample media (also called a membrane herein) 209 that is supported and/or held in place by other components that assist with handling the sample media 209 when it is removed from the device 101 for processing by a laboratory. These other parts of the collection element 250 may include the base 206, a top frame 208, media support 210, and bottom frame 211. The top 208 and bottom 211 frame may have extensions 222A-, 222-B on an outboard end. The extensions 222 further assist with handling the collection element 250 during and after its removal from the housing 101.

The sample media 209 may be a plasma separation membrane or filter of various types located at or near an exit port of the capillaries 105. For example, a mixed-cellulose ester membrane such as the Pall Vivid Plasma Separation available from Pall™ Corporation. The membrane 209 may also be an LF1 glass fiber membrane (sold by General Electric™ Company) or some other media designed to receive serum or whole blood which it then separates into a blood portion and a plasma portion. A media such as LF1 paper has a fibrous structure that causes differential migration of the sample, with a slower rate for red cells, resulting in a gradual separation of plasma sample as it migrates down the paper. The membrane 209 can optionally be previously impregnated with heparin, EDTA, sugars, or other stabilization agents. LF1 paper, which separates plasma from red blood cells through a fiber matrix, is preferred in some embodiments, because it causes a slower migration rate for the blood cells. However other types of separation membranes for blood either liquid or dried may be used.

Plasma separation may also be achieved through non-membrane microstructures that exclude red cells by size. For example, plasma separation can be achieved or enhanced by selectively binding red cells as well. Binding agents are typically coated on a membrane or micro structure but could also be deposited in a channel.

The sample media 209 can also be coated with various chemicals to perform a test, such as an assay, on the collected sample. Thus, an immunoassay strip can be substituted for all, or for part of, or together with the sample media 209. When device 100 is closed, the sample is delivered to a sample pad area on the immunoassay strip. The window 150 may also allow for visual inspection of color change results of the immunoassay or other test.

FIG. 3B is an exploded view of one such example device 100, similar to FIG. 3A. However, this device 100 has both a collection membrane 209 and an immunoassay strip 309. The membrane 209 and strip 309 may be arranged in parallel. The collection membrane 209 receives and stores a blood sample from some capillaries, and the immunoassay (or other test) strip 309 may receive and process a blood sample from other capillaries.

Alternatively, the sample could be delivered to an assay region within the housing 101 where capture molecules are exposed to the sample and bind analytes. These analytes could then be bound by a conjugate making them detectable. The bound analytes may also modify the optical or electrical properties of the surface they are bound to, making them detectable directly.

It can now be appreciated that the action of closing the housing pieces together causes the blood sample to be drawn from the well 104, to be drawn into the capillaries 105 via both capillary action and mechanical force, exiting the capillaries to be deposited onto the sample media 209. In particular, the plungers 202 are engaged by housing piece 201-A, and the capillary tubes 105 are in turn held in place within the inlay 252. Thus, as the housing sections are closed together, the plungers 202 are forced into the capillaries 105, which in turn force blood to exit onto the membrane 209.

In some implementations, the material used to fabricate one or more sections or parts of the inlay piece 252 may have an elasticity that is sufficient to hold the capillary tubes 105 in place while the plungers 202 are forced into them. The elasticity of inlay 252 may also be chosen to seal and/or prevent at least some blood from flowing around, rather than flowing through, the capillary tubes 105.

The closed housing 101 also creates a small and isolated internal air space above the sample media 209. The sample can be further encouraged to dry with the aid of one or more desiccant tablets (not shown) located in this air space. For example, a desiccant may be supported by the backbone 203 adjacent where the sample media 209 sits when the housing is in the closed position.

During or after the housing is closed, a ratcheting mechanism provided by the far end of the backbone 203 encourage the housing to remain shut. For example, the tines 240 may act as a ratcheting pall and engage small holes 245 or other features in the end of housing piece 101-A (See FIG. 1) when the housing is pushed shut. The tines 240 may be shaped to permit opening of the housing only with a pinching tool that accesses small holes 245 in the side of the housing piece 101-B to release the ratchet pawl, e.g. by pinching the tines 240. Thus, once the device 100 is closed by pushing the housing pieces 101-A, 101-B together, the blood sample remains enclosed within, and ready for transport to a remote lab.

Figure 4A:
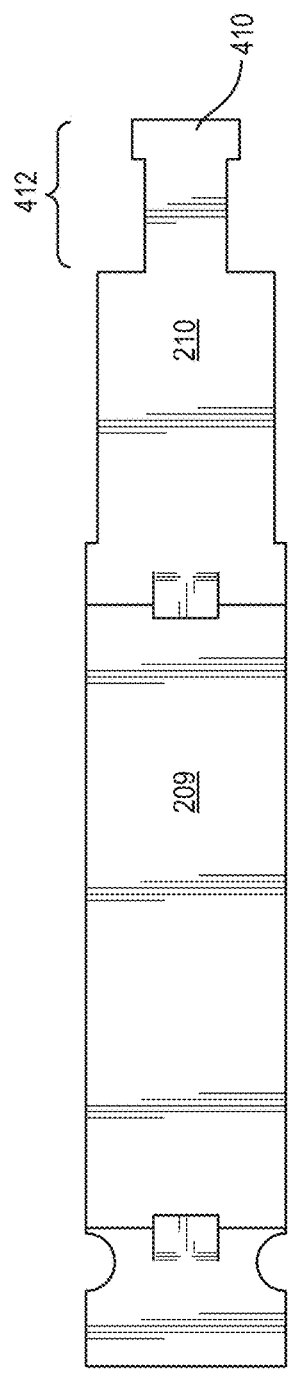
FIGS. 4A and 4B are respective top and side views of one way to implement the sample media and media support.
Figure 4B:
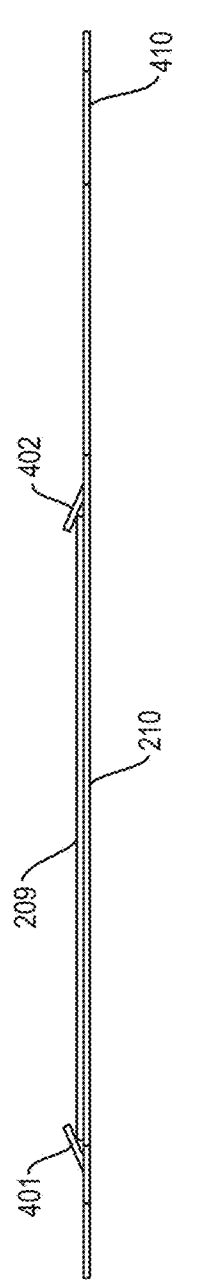
Figure 4C:
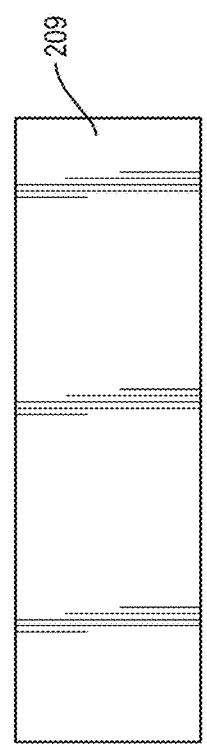
FIG. 4C is a top view of the media and FIG. 4D a top view of the support.
Figure 4D:
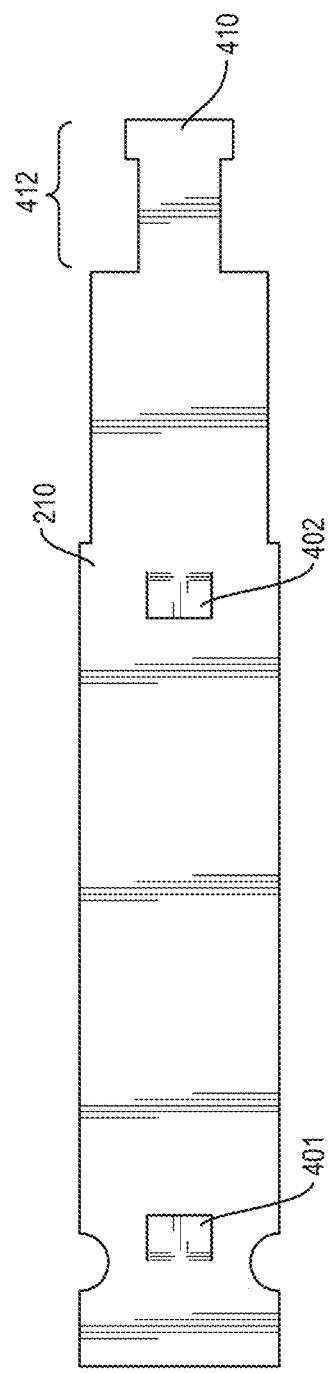

FIGS. 4A and 4B are respective top and side views of one way to implement the sample media 209 and media support 210. FIG. 4C is a top view of the media 209 and FIG. 4D a top view of the support 210.

The media 209 may be a generally rectangular, thin, paper or fibrous, membrane that slips under or fits into tabs 401, 402. Tabs 401, 402 may be cut into or formed as port of support 410 to hold media 209 in place. The support 210 may also have a handle portion 410. The handle 410 may conform to extensions 222 in the frame pieces 208, 211. The handle 410 and makes it easier to handle the collection media 209 when it is removed from the housing 101. The handle 410 may also have other features such as shaped peripheral edges 412 to provide a more secure fit of the support 410 (and/or frame pieces 208, 211) within the housing.

Figure 5:
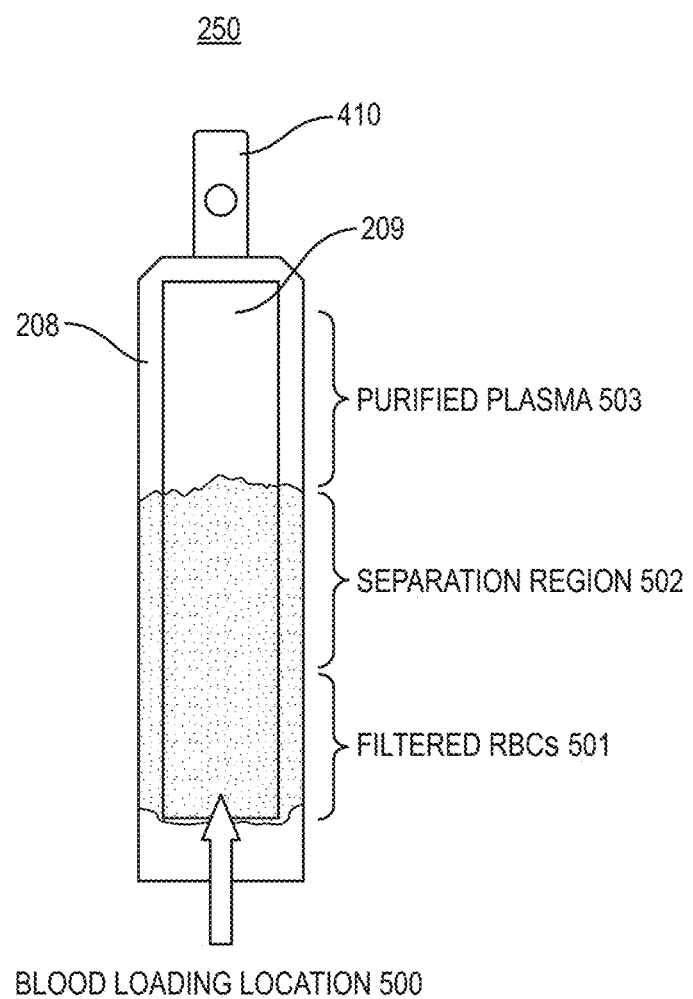
FIG. 5 is a plan view of a sample media.

FIG. 5 is a plan view of a collection element 250 sometime after a blood sample has been taken and after it has been removed from the housing 101. Note a blood loading location 500 that was located adjacent the sample port 102 when the sample was taken. A first region 501 of the sample media 209 contains filtered red blood cells (RBCs). However other portions of the blood sample have diffused through the media 209, to provide a sample separation region 502 and a purified plasma region 503.

Figure 6:
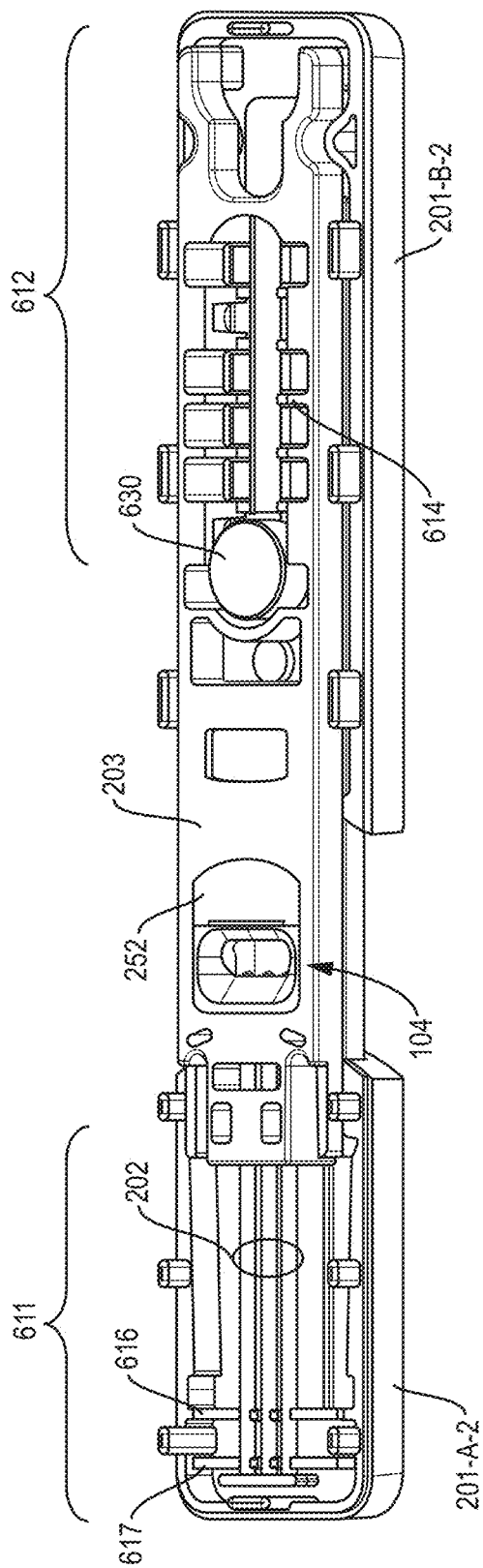
FIG. 6 is a view of the device with the top housing covers removed.

FIG. 6 is a view of the device 100 with both of the top housing covers 201-A-1 and 201-B-1 removed. The backbone 203 is seen to now include not just an area to support the inlay 252 that defines the well 104, but also a plunger support area 611 to the left of the well 104, and a sample media area 612. A ribbed section 614 on the right-hand side includes a generally circular rim that provides support and positioning for one or more tablets of desiccant 630 in FIG. 6 over the sample media area 612. Three plungers 202 are shown on the left-hand side retained in position by a pair of supports 616, 617 in the lower left housing piece 201-A-2. As explained in more detail below, each of the plungers 202 is aligned with a corresponding one of the capillary tubes 204.

Figure 7:
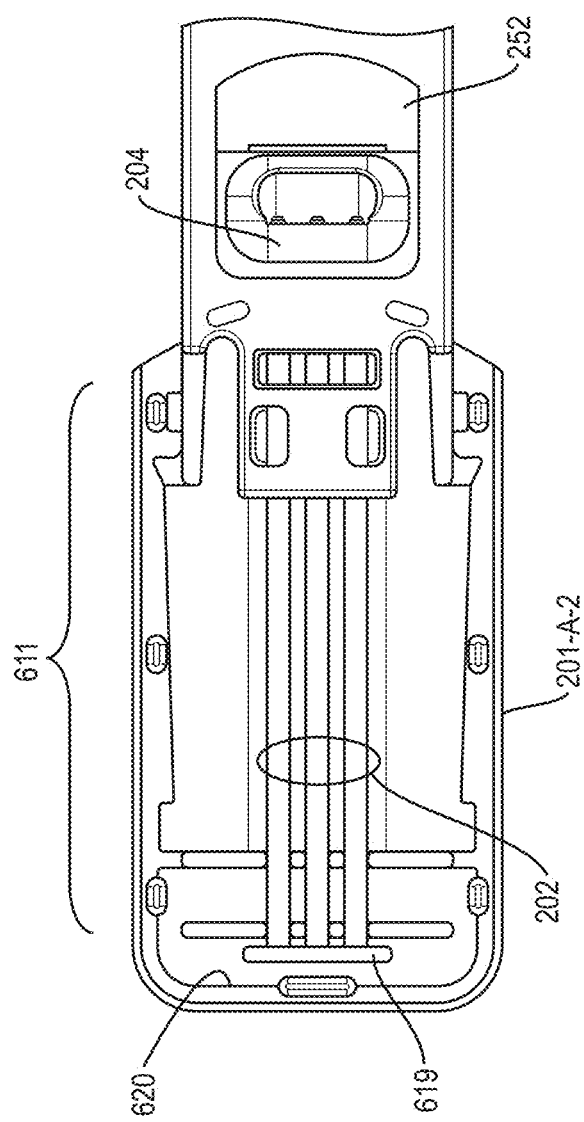
FIG. 7 shows a plunger support area and inlay in more detail.

FIG. 7 shows the plunger support area 611 and inlay piece 252 in more detail. The left ends of the plungers 202 are connected to a tab 619 that rests against an inside edge 620 of the lower housing piece 201-A-2. In this way, the plungers 202 are forced into the capillaries 105 as the housing is closed shut. Note that the right-hand sides of the plungers 202 are inserted into corresponding holes (not shown in FIG. 7) formed in the inlay 252 which are in turn aligned with an inlet of the capillary tubes 204.

FIG. 8 is a partial view of the bottom of part of the support member 203 with the bottom housing covers 201-A-2, 201-B-2 now also removed. Collection media 209 and support 210 have been removed for the sake of illustration in this figure. Ribs 801 on the left end of the support 203 may further assist with guiding the plungers 202 into the inlay 252. Also note a lateral slot 803 is formed on the right-hand side of the inlay 252 adjacent the outlet of the capillary tubes 105. The slot 803 provides an exit path from the capillaries for the collected blood. One or more ridges 820 adjacent slot 803 may further encourage blood exiting the tubes 204 to travel to the lateral slot 803.

FIG. 9 is a partial view of the backside of the inlay 252 similar to FIG. 8, but now with collection element 250 inserted into backbone 203. Note that the position of collection element 250, including frames 208 (and 211, not shown in FIG. 9) hold collection media 209 adjacent the exit path from the capillaries 105 and lateral slot 803.

Figure 10:
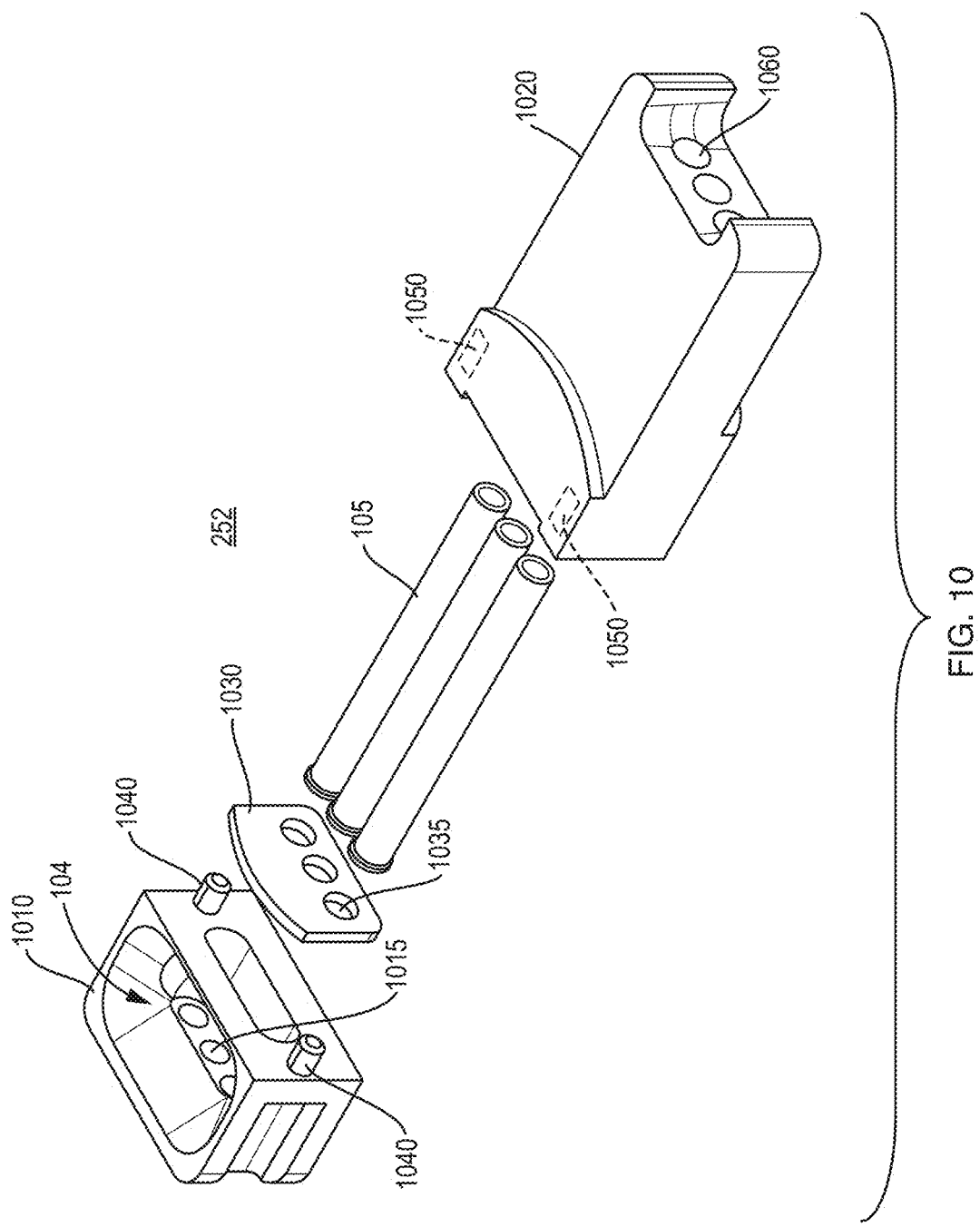
FIG. 10 is an exploded view showing more detail of the components of one example implementation of an inlay.

FIG. 10 is an exploded view showing more detail of the components of one example implementation of an inlay 252.

Figure 11:
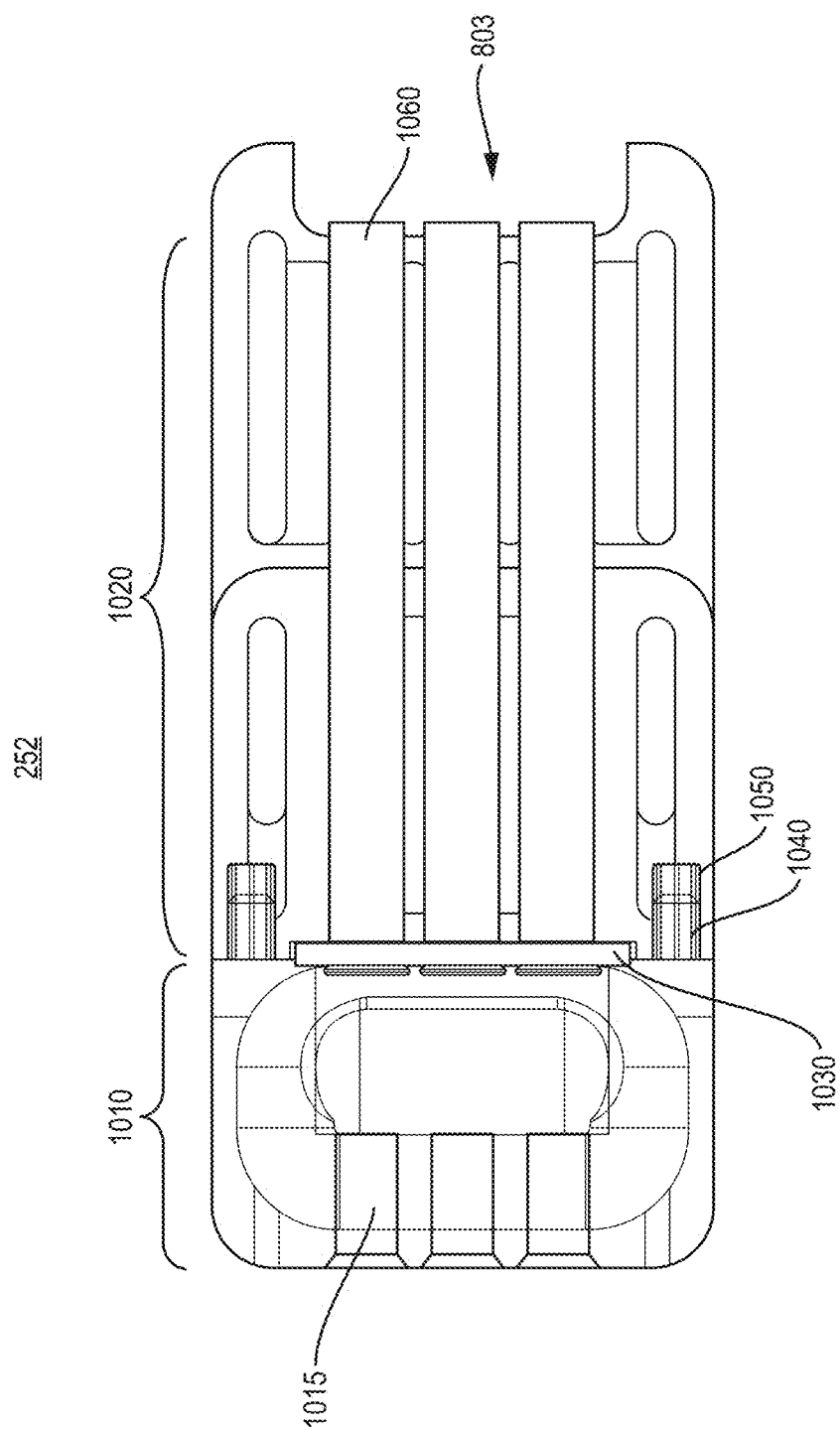
FIG. 11 is a cutaway view of the inlay.

FIG. 11 is a cutaway view of the inlay 252.

Figure 12:
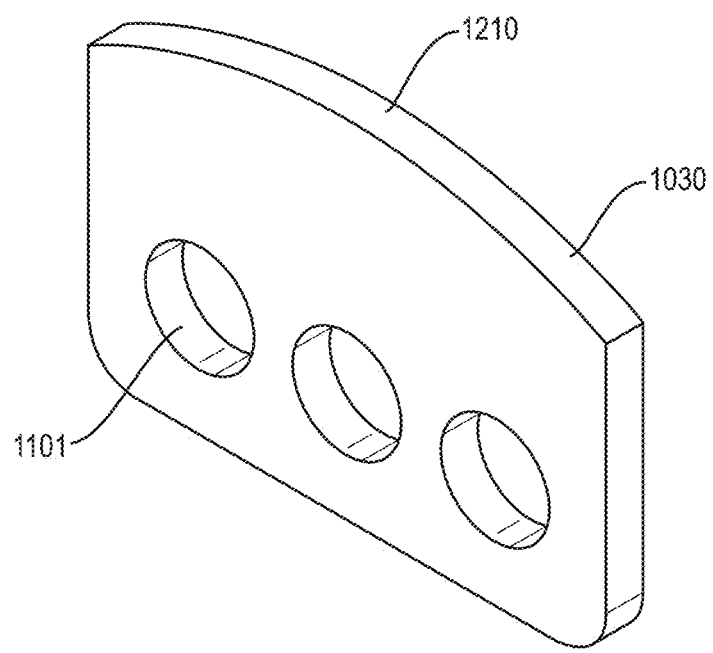
FIG. 12 is a finger swipe ridge.

FIG. 12 is a resilient insert part 1030 of the inlay 252.

In this implementation the inlay 252 consists of three parts, a well piece 1010, a capillary support 1020, and a resilient insert 1030. The well piece 1010 and capillary support 1020 may be formed of a rigid, visually transparent plastic. The inlay 252 may be assembled by engaging pins 1040 on the well piece 1010 into corresponding holes 1050 in the capillary support 1020.

The well piece 1010 generally serves to define the well 104 as a depression or bowl into which the blood sample is initially introduced by the patient. Longitudinal holes 1015 in the well piece 1010 provide guidance for plungers (not shown in FIG. 10).

The capillary support 1020 has longitudinal holes 1060 with a diameter appropriate for firmly holding the capillary tubes 105 in alignment with the plungers (not shown in FIG. 10). Here, three capillaries 105 are supported by the inlay 252, but it is possible to have fewer or a greater number of capillaries 105. Although not seen in this view, capillary support 1020 also defines, in whole or in part, the lateral slot 803 at the exit end of the capillaries.

The insert 1030 is formed of a resilient plastic or rubber. It is disposed between the well piece 1010 and capillary support 1020. The insert 1030 also has a number of holes 1035 formed therein to permit a corresponding number of the capillaries 105 to be inserted through it. Having a generally rectangular shape, insert 1030 preferably has an upper curved ridge 1210. Note the upper ridge on the piece 1101 now provides an edge adjacent the well on which the patient (or a caregiver) can swipe the fingertip to encourage filling the well 1010 with blood.

The ridge on piece 1101 may be treated, coated, or formed of a hydrophobic material, to facilitate blood not sticking thereto and instead being directed to the sample well.

Figure 13:
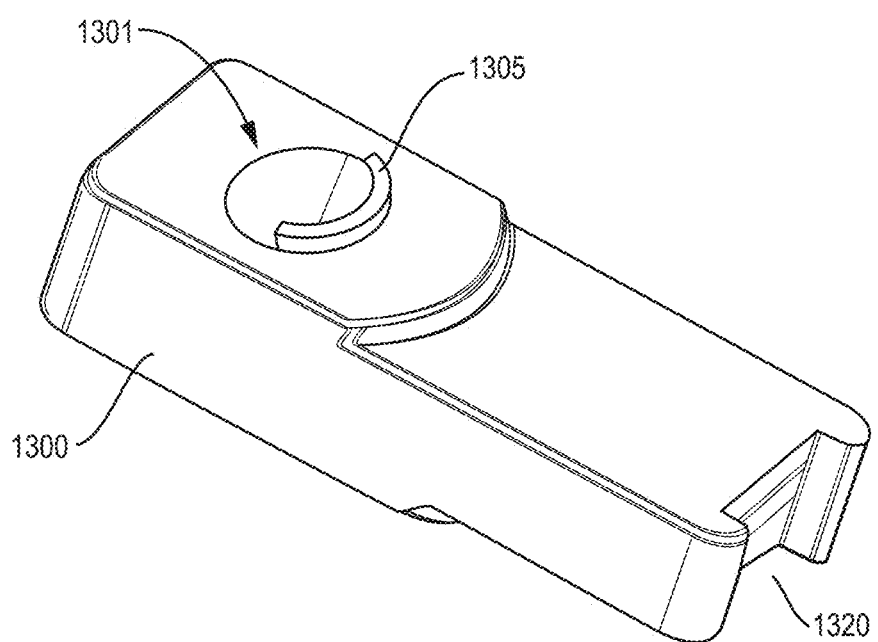
FIG. 13 shows another embodiment of the inlay.

FIG. 13 is a perspective view of an alternate implementation of the inlay 252, here formed from a single piece of resilient material, such as injection molded silicone. This version 1300 of the inlay otherwise has the same features as the inlay 252 version shown in FIG. 10, including at least a sample well 1301, finger swipe ridge 130, and lateral slot 1320.

Figure 14:
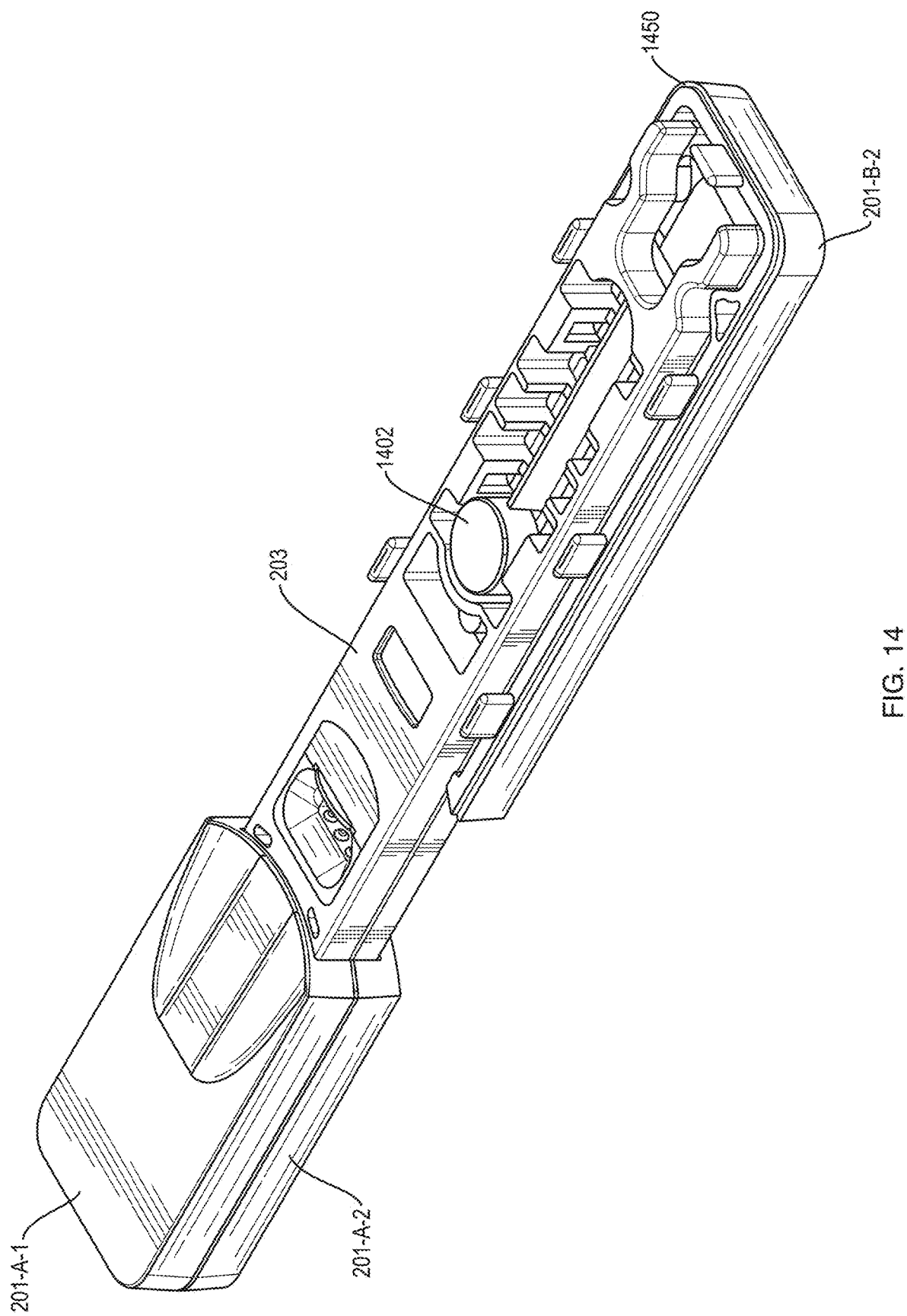
FIG. 14 is a perspective view of the device with a housing cover removed showing a location for a desiccant tablet.

FIG. 14 is a view of the backbone 203 with housing covers removed, showing one possible location of a desiccant 1402 in tablet form. Note the tablet 1402 is held in place above the sample media 209 such as near the exit end of the capillaries (not shown in FIG. 14). Although only one desiccant tablet 1402 is shown, certainly more than one may be provided. Also note here that one corner 1450 of one or more of the housing pieces, for example, housing piece 201-B-2, may have a shape that is different from the other corners of the other housing pieces 101. For example, corner 1450 may be chamfered while the other corners are rounded. Corner 1450, having a different shape, may assist with registration of the device 100 with automated handling or processing equipment.

Figure 15:
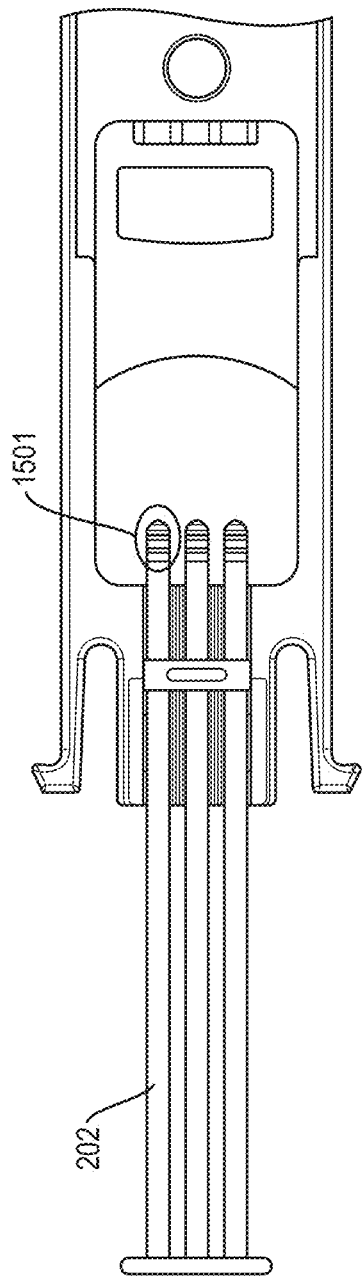
FIG. 15 is another view of a portion of a backbone and plungers.

FIG. 15 is a close up view of the plungers 202, illustrating that the ends 1501 thereof may be ribbed or castellated, to further promote blood flow into and through the capillaries 105.

Figure 16:
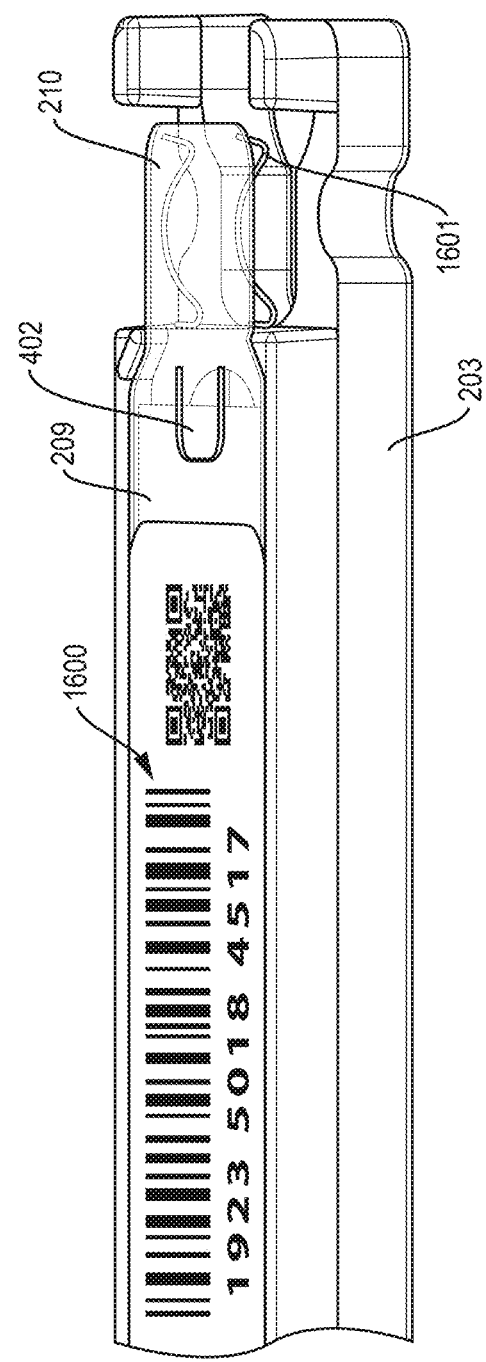
FIG. 16 is a detailed view of a clip holding a collection element.

FIG. 16 is a detailed view of one way to further hold the collection element 250 within backbone 203, via one or more spring clips 1601. The clips 1601 may engage or press against one end of the media support 210. The clips 1601 may also engage other corresponding features in the backbone 203 or housing pieces 201-B-2 (not shown). Note that a barcode 1600 or other identifying indicia such as a QR code, or reference number, may be printed on or on a label affixed to a back side of the collection element 250.

In use, the device 100 is a very convenient way to collect blood expressed by a patient after using a lancet on one of his/her fingers. Commercially-available lancets may be used, and it generally is the choice of the user to select the type of lancet. Once a drop of blood has been expressed on the finger, the patient skims the drop into a well 104 in the sample collection port 102 by gliding the finger across the protruding resilient edge 1030. The blood drop, through gravitational force and surface forces, proceeds to the bottom of the well 104 where it encounters openings in the collection (metering) capillaries 105. From there, blood is further drawn into the collection element 250 including the sample storage media 209, further encouraged by plungers that force blood out of the capillaries as the two housing pieces are closed together.

The closed device 100 then creates a small and isolated internal air space which can be quickly dried with the aid of desiccant tablets contained in an internal pocket. In its current form, use of LF1 paper as a collection media creates spots of red-cell free plasma as well as plasma-depleted whole blood. The LF1 paper's structure causes differential migration, with a slower rate for red cells, resulting in a gradual separation of plasma sample the further down the paper the sample migrates. Plasma is far better for any quantitative blood test, eliminating red cells, which tend to interfere with many analyte assays.

The device 100 therefore offers substantially better opportunity for high-quality quantitative assays as compared to standard dried blood spots. Furthermore, infectious disease tests can still be done on the red cell portion of the dried sample—though plasma-depleted, it is still adequate for accurate detection of infectious agents.

The device is also an ideal mechanism for blood sample preservation and transport. Once the device is closed, the blood sample is enclosed within, largely cut off from the external environment. Upon closing by the user, the device uses the ratcheting mechanism to ensure it remains locked and shut. It can be opened only with the use of a pinching tool that accesses the small holes 245 in the side of the housing 101 to releases the ratchet pawl.

Observations

A. Device that Collects, Stabilizes, and Stores a Predetermined Amount of Body Fluid
  i) It is now understood that a fluid sample collection device may include a housing configurable from an open position to a closed position; a sample collection well for collecting fluid; one or more capillaries, arranged to draw in fluid from the sample collection well through capillary action, the capillaries having a predetermined volume; a membrane; one or more plungers, disposed in line with the capillaries and arranged to dispense fluid from the capillaries onto the membrane when the housing is moved from the open to the closed position; and a fluid stabilization agent, arranged to engage the fluid as the one or more plungers dispense fluid onto the membrane.
  ii) The stabilization agent may be heparin and/or EDTA, or coated onto an interior of at least one of the capillaries, or coated onto the membrane.
  iii) A removable support element, may be disposed within the housing, for supporting the membrane in place adjacent an exit port of the capillaries.
  iv) The housing may additionally include a desiccant region adjacent the membrane. A desiccant may be a tablet; and a structure such as a backbone or skeleton may hold the desiccant tablet in a defined position adjacent the membrane.
  v) One or more of the capillaries may be coated with a reagent, or hold a predetermined amount of a liquid reagent. The storage membrane may contain the reagent.
  vi) The membrane may a testing strip in part or in whole, such an immunoassay strip. Such a test strip may be disposed in-line with an exit port of one of the capillaries. The test strip may be some other type of assay disposed on or adjacent to the whole blood collection membrane.
  vii) A stored reagent may be mixed with the fluid when the housing is moved from the open position to the closed position.
  viii) A ridge portion may be disposed adjacent the sample well. It may be hydrophobic.
  ix) A collection element disposed within the housing, may further include a depression formed therein to provide the sample well; and a raised ridge portion formed adjacent the depression and extending along only a portion an outer edge of the depression. The depression may be circular.

B. Window to View Progress of Sample Well and/or Capillaries and/or Assay
  i) It is also understood now that a fluid sample collection device may include a housing configurable from an open position to a closed position; a sample collection well, disposed within the housing, for collecting fluid; one or more capillaries, arranged to draw in fluid from the sample collection well through capillary action, the capillaries having a predetermined volume; a membrane; one or more plungers, disposed in line with the capillaries and arranged to dispense fluid from the capillaries onto the membrane when the housing is moved from the open to the closed position, and wherein the sample well is visible and exposed to receive the fluid when the housing is in the open position; wherein the housing at least partially encloses the sample well when the housing is in the closed position; and an optically transparent window, located within the housing, provides a view of at least a portion of the sample well and/or at least one of the capillaries and/or the membrane when the housing is in either the open or the closed position.
  ii) The window may be located adjacent the capillaries.
  iii) The capillaries may be visibly transparent, so that when the housing is in the open position, the capillaries provide a visible indication that a sample of fluid is being collected by the device.
  iv) In addition, when the housing is in the closed position, the optically transparent window may provide an indication whether a sufficient sample of fluid was drawn into the device.
  v) The device may include a first housing section and second housing section engaged and are slidable along a center support section, to allow moving the housing from the open position to the closed position.
  vi) The center support section may include the sample well.
  vii) In some arrangements, the first housing piece includes an optically transparent window arrange to provide a view of one or more capillaries when the housing is the closed position.
  viii) The center support section may hold the capillaries in fixed alignment with the optically transparent window.
  ix) In some configurations, the membrane provides one or more of a sample storage region or an assay region.

C. Inlay Element Provides Alignment and Support for Capillaries
  i) It is also now appreciated that a fluid sample collection device may include a housing configurable from an open position to a closed position; a sample collection well, disposed within the housing, for collecting fluid; one or more capillaries, arranged to draw in fluid from the sample collection well through capillary action, the capillaries having a predetermined volume; a sample storage membrane; one or more plungers, disposed in line with the capillaries and arranged to dispense fluid from the capillaries onto the membrane when the housing is moved from the open to the closed position; and a support element or so-called "inlay" disposed within the housing to retain at least one capillary in alignment with at least one of the plungers as the housing is moved from the open position to the closed position.

ii) The support element may further include one or more holes, each for engaging a respective one of capillaries.
iii) All or part of the support element may be formed of a resilient material.
iv) The device may be configured such that two or more of the plungers are connected to a tab attachment on an end distal from the capillaries.
v) The housing may comprise a first housing section and second housing section, with the housing being in the open position when the two sections are spaced apart from one another, and the housing being in the closed position when the two housing sections are moved adjacent one another.
vi) In certain configurations, a tab attachment is disposed in mechanical communication with the first housing section, such that as the two housing sections are moved adjacent one another, the plungers also move and force fluid through the capillary tubes.
vii) The support element may further comprise a slot disposed at an exit port of the one or more capillaries. Such a slot may be disposed to further direct fluid from the capillaries towards the sample storage membrane.
viii) A lateral flange may be disposed adjacent the capillaries and the slot to further encourage fluid to pass to the lateral slot.
ix) In addition, the plungers may further each include a circumferential seal.
x) The support element may be visually transparent.

D. Pinch to Open for Access to Membrane i) In other configurations, a fluid sample collection device includes a housing configurable from an open position to a closed position; a sample collection well for collecting fluid; one or more capillaries, arranged to draw in fluid from the sample collection well through capillary action, the capillaries having a predetermined volume; a membrane; one or more plungers, disposed in line with the capillaries and arranged to dispense fluid from the capillaries onto the membrane when the housing is moved from the open to the closed position; a removable support element disposed within the housing and providing support for the membrane; and an opening in the housing to enable access to the membrane.
ii) A fluid stabilization agent may be deposited in at least one of the capillaries or on the membrane.
iii) The removable support element may include a ratcheting mechanism that is engaged when the housing is moved from the open to the closed position.
iv) In such a case, the housing includes one or more access openings adjacent the ratcheting mechanism.
v) Furthermore, the ratcheting mechanism may comprise a pawl that is releasable via the one or more access openings.

E. Mylar Substrate with Tabs for Membrane i) It is also understood how fluid sample collection assembly includes a substrate having a pair of engagement tabs therein and spaced apart from one another; and a blood sample collection region, located adjacent the substrate and sized to fit between the engagement tabs.
ii) The substrate may be formed of mylar.
iii) In some configurations, the engagement tabs are formed by cutting slots in the substrate.
iv) The membrane may be a strip of LF1 paper, Pall membrane, or a bound glass fiber filter, or other membrane to separate serum or whole blood into a blood portion and a plasma portion.
v) The membrane can also be treated with heparin, EDTA, sugars, or other stabilization agents.
vi) Here, also, the housing can be re-configurable from an open position to a closed position, or have a sample collection well for collecting fluid; or include one or more capillaries, arranged to draw in fluid from the sample collection well through capillary action, the capillaries having a predetermined volume; or one or more plungers, disposed in line with the capillaries and arranged to dispense fluid from the capillaries onto the membrane when the housing is moved from the open to the closed position.

Therefore, it should be understood that in light of the above, various modifications and additions may be made to the device without departing from the true scope of the inventions made.

The invention claimed is:

1. A blood sample collection device comprising:
a housing configurable from an open position to a closed position;
a sample collection well;
two or more capillaries configured to draw in fluid from the sample collection well through capillary action;
a membrane disposed within the housing;
a plunger rack comprising two or more plungers, wherein the plunger rack is disposed within the housing, and wherein the two or more plungers comprise two or more ends disposed in line with the two or more capillaries and arranged to dispense the fluid in the two or more capillaries onto the membrane when the housing is moved from the open position to the closed position; and
a desiccant region disposed adjacent to the membrane.

2. The device of claim 1, further comprising a backbone structure, disposed within the housing, at least a part of which extends into the desiccant region.

3. The device of claim 2, wherein the backbone structure supports a desiccant tablet.

4. The device of claim 2, wherein the backbone structure comprises a rim within the desiccant region; and a desiccant tablet disposed within the rim.

5. The device of claim 1, further comprising a removable support element disposed within the housing and providing support for the membrane.

6. The device of claim 1, wherein the desiccant region is positioned adjacent to an end of the two or more capillaries.

7. The device of claim 1, wherein at least one of the two or more capillaries or the membrane comprise heparin, EDTA, sugars, or another fluid stabilization agent.

8. The device of claim 1, wherein an interior surface of the two or more capillaries comprises heparin.

9. The device of claim 1, wherein the device is configured to lock in the closed position.

10. The device of claim 9, further comprising an aperture to release a ratchet pawl thereby configured to unlock the device from the closed position.

11. The device of claim 1, wherein the two or more ends of the plunger rack are ribbed or castellated to promote blood flow through the capillaries.

12. The device of claim 1, wherein the membrane comprises a plasma separation membrane.

13. The device of claim 1, wherein the membrane comprises heparin, EDTA, sugars, or other stabilization agents.

14. The device of claim 1, wherein the housing comprises a first housing piece and a second housing piece which slide with respect to one another when the housing is moved from the open position to the closed position.

15. The device of claim 1, wherein the membrane comprises LF1 paper, bound glass fiber filter, or other membrane material to separate serum or whole blood into a blood portion and a plasma portion.

16. The device of claim 1, further comprising three or more capillaries configured to meter a volume of the blood sample.

17. The device of claim 16, wherein the plunger rack further comprises three or more plungers, wherein the plunger rack is disposed within the housing, and wherein the three or more plungers comprise three or more ends disposed in line with the three or more capillaries and are arranged to dispense the fluid in the three or more capillaries onto the membrane when the housing is moved from the open position to the closed position.

18. The device of claim 1, further comprising a transparent window in the housing configured to view the two or more capillaries.

19. The device of claim 1, further comprising an isolated internal air space within the housing when the housing is in the closed position.

* * * * *